US011298139B2

(12) United States Patent
Voros

(10) Patent No.: US 11,298,139 B2
(45) Date of Patent: Apr. 12, 2022

(54) TOURNIQUET BELT

(71) Applicant: Eric Matthew Voros, Medford, NJ (US)

(72) Inventor: Eric Matthew Voros, Medford, NJ (US)

( * ) Notice: Subject to any disclaimer, the term of this patent is extended or adjusted under 35 U.S.C. 154(b) by 0 days.

(21) Appl. No.: 16/687,216

(22) Filed: Nov. 18, 2019

(65) Prior Publication Data

US 2020/0237379 A1 Jul. 30, 2020

Related U.S. Application Data

(60) Provisional application No. 62/796,653, filed on Jan. 25, 2019.

(51) Int. Cl.
*A61B 17/132* (2006.01)
*A61B 17/00* (2006.01)

(52) U.S. Cl.
CPC *A61B 17/1327* (2013.01); *A61B 2017/00407* (2013.01)

(58) Field of Classification Search
CPC ...... A61B 17/1327; A61B 2017/00407; A61B 17/132; A61B 17/1322; A61B 17/1325
USPC ........................................ 606/201, 203, 204
See application file for complete search history.

(56) References Cited

U.S. PATENT DOCUMENTS

| | | | | |
|---|---|---|---|---|
| 8,888,807 B2 * | 11/2014 | Esposito | ............ | A61B 17/1327 606/203 |
| 9,750,507 B2 * | 9/2017 | Brub | .................. | A61B 17/1327 |
| 2010/0057120 A1 * | 3/2010 | Kirkham | ............ | A61B 17/1322 606/203 |
| 2018/0153557 A1 * | 6/2018 | Dimino | .................... | A61B 5/03 |

* cited by examiner

*Primary Examiner* — Tan-Uyen T Ho
*Assistant Examiner* — Bridget E. Rabaglia
(74) *Attorney, Agent, or Firm* — FisherBroyles, LLP; Christopher R. Kinkade; Craig W. Mueller

(57) ABSTRACT

A tourniquet belt system is provided. The tourniquet belt system includes a belt strap component which includes a front layer and a rear layer. The front layer and the rear layer are coupled to each other using a belt strap fastening mechanism. The tourniquet belt system further includes a tourniquet component, concealed between the front layer and the rear layer, which includes a tourniquet layer secured to an inner portion of the belt strap component and which runs along a length of the belt strap. The tourniquet belt system additionally includes a tightening rod. A portion of the tourniquet layer is coupled to the tightening rod for decreasing a length of the tourniquet layer within the belt strap component. The tourniquet system further includes a buckle component, which includes a buckle fastening mechanism and a ratchet mechanism configured to secure the belt strap component around a surface.

17 Claims, 3 Drawing Sheets

500

```
┌─────────────────────────────────────────────┐
│   TOURNIQUET BELT SYSTEM UNFASTENED         │
│                   505                       │
└─────────────────────────────────────────────┘
                     │
                     ▼
┌─────────────────────────────────────────────┐
│   BELT STRAP WRAPPED AROUND WOUNDED AREA    │
│                   510                       │
└─────────────────────────────────────────────┘
                     │
                     ▼
┌─────────────────────────────────────────────┐
│   BELT STRAP PULLED THROUGH RATCHET MECHANISM │
│                   515                       │
└─────────────────────────────────────────────┘
                     │
                     ▼
┌─────────────────────────────────────────────┐
│ FRONT AND REAR LAYERS SEPARATED TO REVEAL TIGHTENING ROD │
│                   520                       │
└─────────────────────────────────────────────┘
                     │
                     ▼
┌─────────────────────────────────────────────┐
│ TIGHTENING ROD TWISTED TO CONSTRICT BLOOD FLOW TO │
│               WOUNDED AREA                  │
│                   525                       │
└─────────────────────────────────────────────┘
```

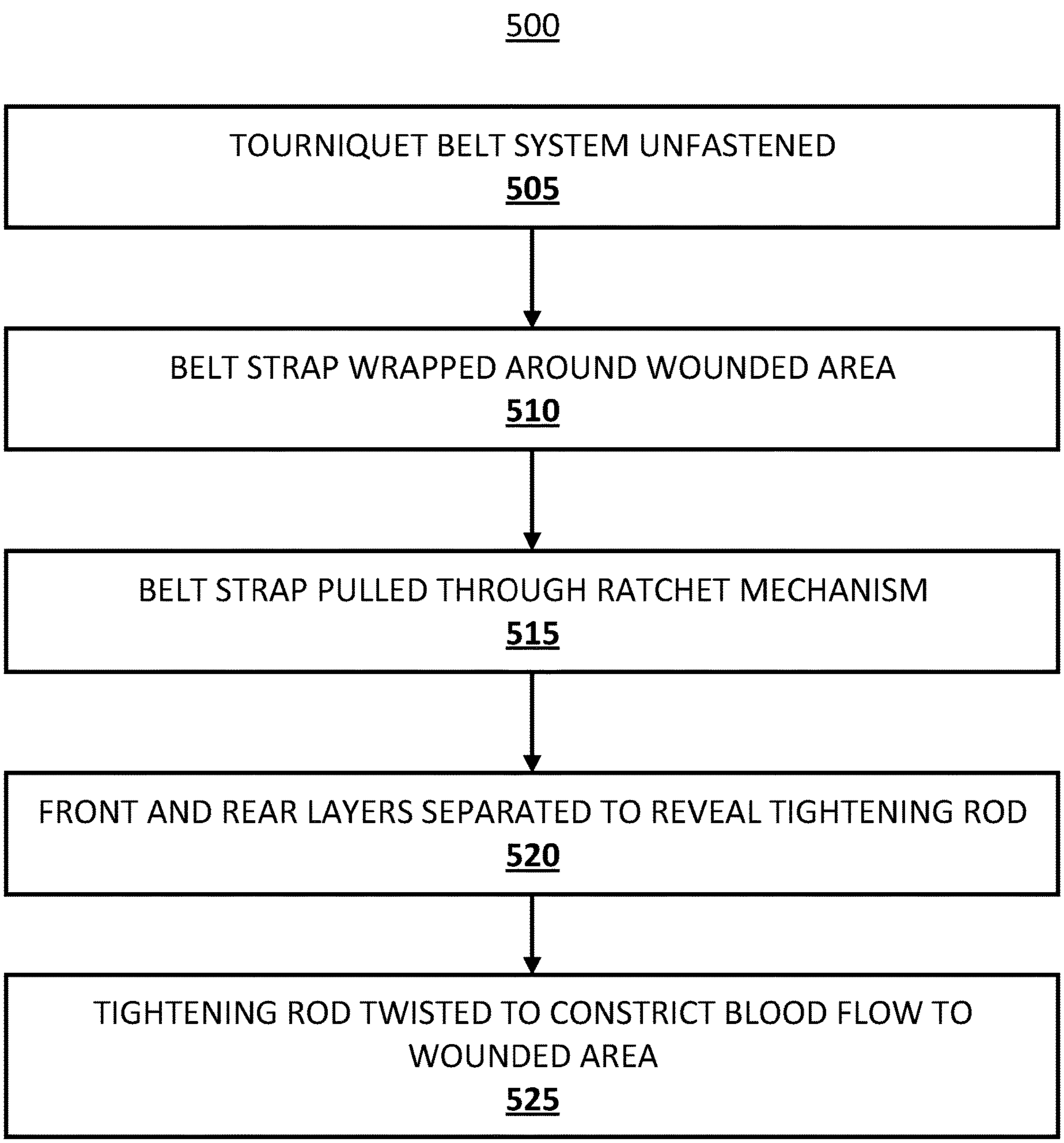

FIG. 5

TOURNIQUET BELT

CLAIM OF PRIORITY

This application is a United States non-provisional patent application and claims priority to U.S. provisional patent application No. 62/796,653, filed Jan. 25, 2019, herein incorporated by reference in its entirety.

FIELD OF THE INVENTION

The present disclosure relates to tourniquet devices and, in particular, to a belt that incorporates an integrated tourniquet and which combines and integrates the functionality of belts and the functionality of a tourniquet medical device.

BACKGROUND

Injuries often occur that result in blood loss. For many of these injuries, the application of pressure to the wound often effectively stops the bleeding and enables the injured person to properly heal. However, for many injuries, mere pressure does not prevent blood loss and a tourniquet is needed to prevent further blood loss. For these reasons, a tourniquet is a life saving medical device. However, unlike adhesive bandages, gauze, or other common first aid items, tourniquets are not often carried by the average person or kept in a general first aid kit. Therefore, in many instances where a tourniquet is needed, there is not one to be found, resulting in further blood loss and/or death of the injured person.

Due to the lifesaving uses of tourniquets, it is of great importance that ready access to them be available to the average person for easy access in the event that a tourniquet is needed. However, due to the elongated shape of tourniquets, it is difficult for the average person to easily carry and conceal a tourniquet during normal day-to-day activities. Therefore, a discrete and simplified means of transporting a tourniquet during the regular activities of an average person is thus needed.

SUMMARY

According to an aspect of the present disclosure, a tourniquet belt system is provided. The tourniquet belt system includes a belt strap component which includes a front layer and a rear layer. The front layer and the rear layer are coupled to each other using a belt strap fastening mechanism. The tourniquet belt system further includes a tourniquet component, concealed between the front layer and the rear layer. The tourniquet component includes a tourniquet layer secured to an inner portion of the belt strap component. The tourniquet layer runs along a length of the belt strap. The tourniquet belt system additionally includes a tightening rod. A portion of the tourniquet layer is coupled to the tightening rod such that twisting the tightening rod decreases a length of the tourniquet layer within the belt strap component. Furthermore, the tourniquet system includes a buckle component. The buckle component includes a buckle fastening mechanism for fastening the belt strap around a user, and a ratchet mechanism configured to secure the belt strap component around a surface.

In some embodiments, the buckle component further includes a quick release mechanism configured to separate the buckle fastening mechanism from the belt strap component.

In some embodiments, the front layer includes leather.

In some embodiments, the belt strap component further includes a compartment for concealing the tightening rod.

In some embodiments, the front layer and the rear layer are configured to separate as a location of the compartment, enabling the user to access the tightening rod.

In some embodiments, the tourniquet layer includes a nylon strap.

In some embodiments, the belt strap fastening mechanism is selected from the group consisting of one or more snap fasteners, one or more hook and loop fasteners, and thread.

In some embodiments, the belt strap component include one or more holes configured to receive a portion of the buckle fastening mechanism.

In some embodiments, the front layer includes an outer securing mechanism configured to enable an equipment layer to be fastened against an outer portion of the front layer.

According to another aspect of the present disclosure, a method for applying a tourniquet is provided. The method includes unfastening a tourniquet belt system. The tourniquet belt system includes a belt strap component which includes a front layer and a rear layer. The front layer and the rear layer are coupled to each other using a belt strap fastening mechanism. The tourniquet belt system further includes a tourniquet component, concealed between the front layer and the rear layer. The tourniquet component includes a tourniquet layer secured to an inner portion of the belt strap component. The tourniquet layer runs along a length of the belt strap. The tourniquet belt system additionally includes a tightening rod. A portion of the tourniquet layer is coupled to the tightening rod such that twisting the tightening rod decreases a length of the tourniquet layer within the belt strap component. Furthermore, the tourniquet system includes a buckle component. The buckle component includes a buckle fastening mechanism for fastening the belt strap around a user, and a ratchet mechanism configured to secure the belt strap component around a surface. The method further includes wrapping the belt strap component around a wounded area of a patient, and pulling a first end of the belt strap component through the ratchet mechanism, forming a tight seal around the wounded area. The method additionally includes twisting the tightening rod, constricting the wounded area.

In some embodiments, the buckle component further includes a quick release mechanism configured to separate the buckle fastening mechanism from the belt strap component, and the unfastening the tourniquet belt system from the user includes applying the quick release mechanism in order to separate the buckle fastening mechanism from the belt strap component.

In some embodiments, the belt strap component further includes a compartment for concealing the tightening rod.

In some embodiments, the front layer and the rear layer are configured to separate as a location of the compartment, enabling the user to access the tightening rod.

In some embodiments, the method for applying the tourniquet further includes separating the front layer and the rear layer at the location of the compartment, revealing the tightening rod.

In some embodiments, the tourniquet layer includes a nylon strap.

In some embodiments, the belt strap fastening mechanism is selected from the group consisting of one or more snap fasteners, one or more hook and loop fasteners, and thread.

In some embodiments, the belt strap component include one or more holes configured to receive a portion of the buckle fastening mechanism.

BRIEF DESCRIPTION OF THE DRAWINGS

FIG. 5 is a flowchart of an example of a method for using a tourniquet belt system, in accordance with an embodiment of the present disclosure.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. When used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

Other terms that are relevant to this disclosure are defined at the end of this Detailed Description section.

Figure 1:
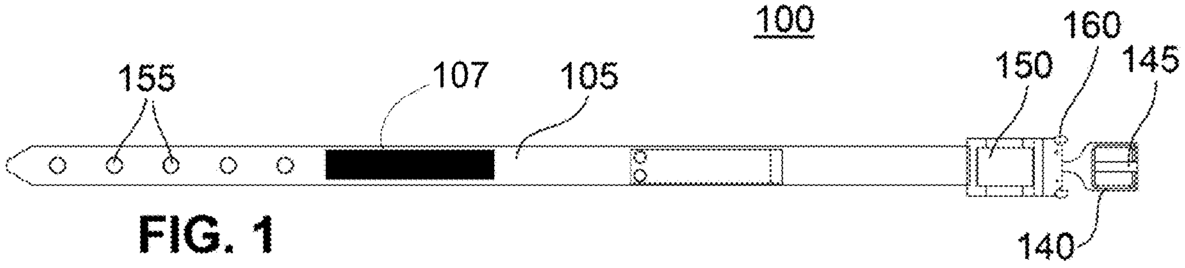
FIG. 1 is an example of an upper view of a tourniquet belt system, in accordance with an embodiment of the present disclosure.
Figure 2:
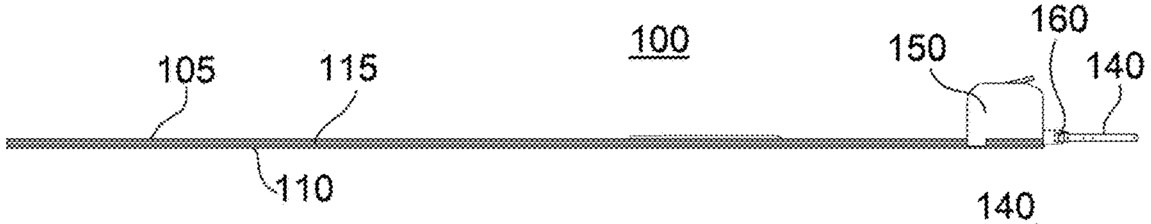
FIG. 2 is an example of a side view of a tourniquet belt system, in accordance with the present disclosure.
Figure 3:
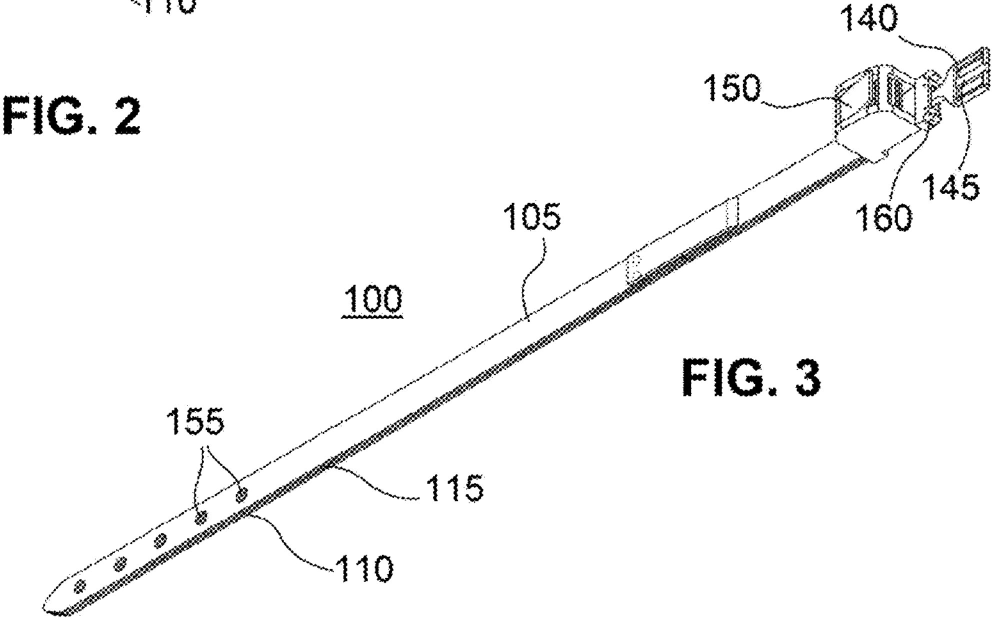
FIG. 3 is an example of a perspective view of a tourniquet belt system, in accordance with the present disclosure.

Referring now to FIGS. 1-3, a top view (FIG. 1), a side view (FIG. 2), and a perspective view (FIG. 3) of a tourniquet belt system 100 incorporating a functional tourniquet into a wearable belt is provided. By incorporating a tourniquet into a wearable belt, the tourniquet belt system 100 enables lifesaving tourniquets to be easily worn and readily and quickly available to the average person who wears a belt.

According to an embodiment, the tourniquet belt system 100 includes a front layer 105 and a rear layer 110. According to an embodiment, the front layer 105 and the rear layer 110 are affixed together. This results in composite belt strap component formed by the joining of the front layer 105 and the rear layer 110 to outwardly appear similar to a common belt, enabling the user to wear the tourniquet around his/her waist in a similar fashion to that of a person wearing a standard belt. The front layer 105 and the rear layer 110 may be affixed to each other via a belt strap fastening mechanism, which may include an adhesive, a thread-based connection 125 (for example, being sewn together), one or more snap fasteners 130, one or more hook and loop fasteners, one or more magnets, one or more zippers, and/or via any other suitable affixing means.

Figure 4:
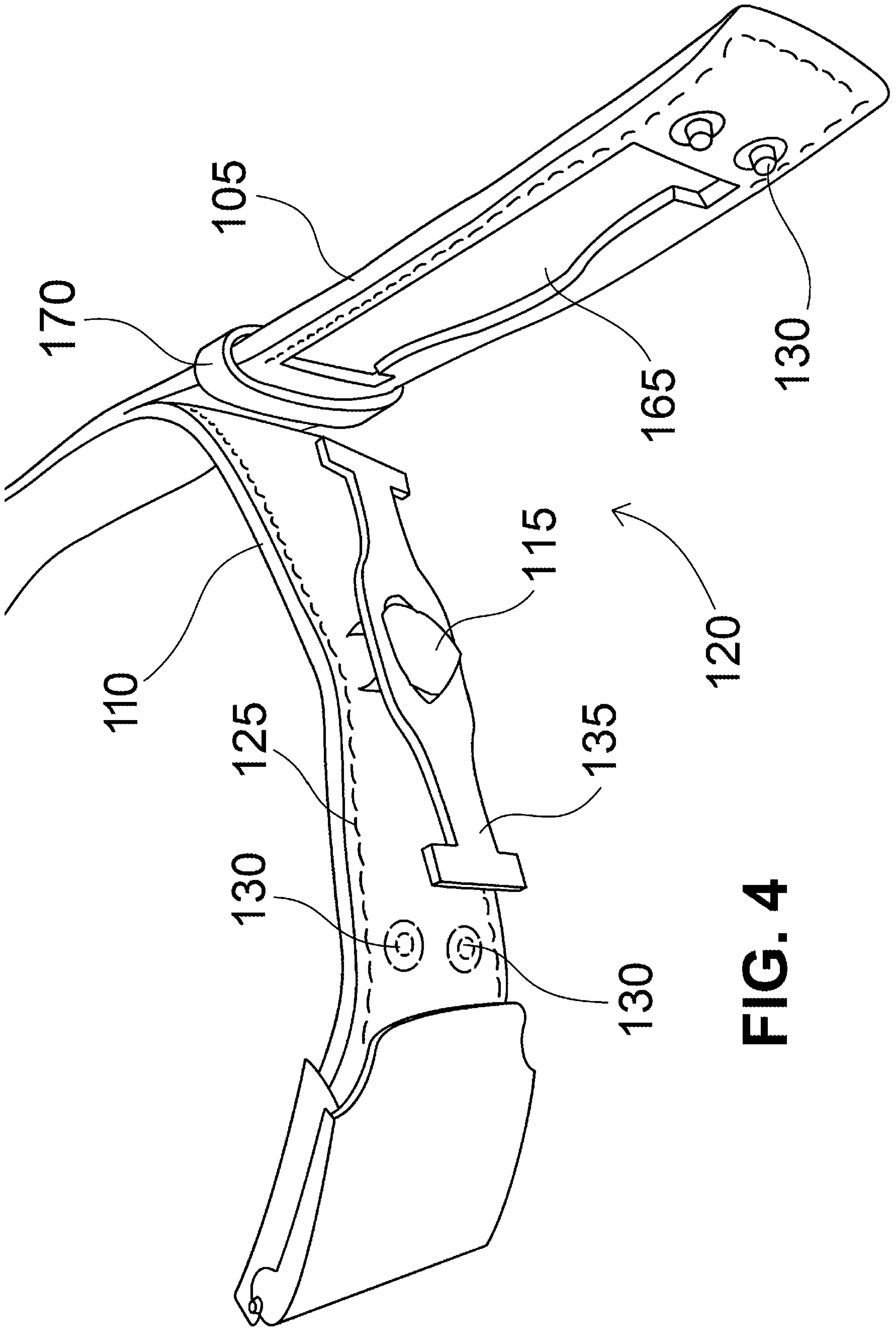
FIG. 4 is an example of a tourniquet belt system having a front layer and a rear layer separated, in accordance with the present disclosure.

According to an embodiment, a tourniquet component 120 (as shown in FIG. 4) is positioned and concealed between the front layer 105 and the rear layer 110. The tourniquet component 120 may be permanently affixed between the front layer 105 and the rear layer 110 or may be removably affixed between the front layer 105 and the rear layer 110.

According to an embodiment, the front layer 105 is the visible component when the tourniquet belt system 100 is worn by a user. The front layer 105 may have the appearance of a wearable belt. This enables a user wearing the tourniquet belt system 100 to wear the tourniquet component 120 around his/her waist in a similar fashion to that of a person wearing a standard belt. The front layer 105 may include leather, fabric, synthetic leather, and/or any other suitable component to enable the front layer 105 to appear similar to a wearable belt.

The tourniquet component 120 includes a tourniquet layer 115 configured to act as a tourniquet. According to various embodiments, the tourniquet layer 115 is a fabric layer. According to various embodiments, the tourniquet layer 115 is a nylon strap. It is noted, however, that any material suitable for use as a tourniquet may be used as the tourniquet layer 115. According to an embodiment, the tourniquet component 120 includes a tightening rod 135. The tightening rod 135 may be of any size, shape, and material suitable for tightening the tourniquet layer 115 and also capable of being concealed by the front layer 105 to enable the system to be worn as a traditional belt. In preferred embodiments, the tightening rod 135 is an elongated rod or bar made from metal, carbon fiber, fiberglass, hardened plastic, polymer or polymer blends, and/or any other suitable material capable of withstanding the force of tightening the tourniquet. The tourniquet layer 115 is affixed to or wraps around the tightening rod 135, forming a Spanish windlass mechanism, enabling the tourniquet layer 115 to tighten around a desired area, constricting blood flow. According to various embodiments, when affixed inside the front layer 105 and rear layer 110, the tourniquet layer 115 is sewn in place at the ends between the front layer 105 and the rear layer 110. According to a preferred embodiment, the tourniquet layer 115 is sewn in place only at its distal ends and not along the length of the front layer 105 and the rear layer 110, allowing the tourniquet layer 115 to move freely between the front layer 105 and the rear layer 115 to facilitate better constriction when the tourniquet is used.

According to various embodiments, the rear layer 110 includes a soft fabric. It is noted, however, that any suitable material for use with a belt, for the section of the belt which abuts against the body of the wearer of the belt, may be used as the rear layer 110, while maintaining the spirit of the present disclosure. According to a preferred embodiment, the rear layer 110 includes a fabric which, when pressed against the tourniquet layer 115, maintains a position of the tourniquet layer 115 while enabling the tourniquet layer 115 to move independent from the front layer 105. According to various embodiments, the rear layer 110 may act as a padding component when the tourniquet belt system 100 is used as a tourniquet. This padding acts as a barrier between the tourniquet layer 115 and a patient on which the tourniquet is used, aiding in the prevention of the tourniquet layer 115 from pinching and/or otherwise damaging the skin of the patient. According to various embodiments, the rear layer 110 enables the tourniquet belt system 100 to apply relatively uniform contact and pressure along the length of the tourniquet belt system 100 while in use as a tourniquet.

According to an embodiment, the tourniquet belt system 100 includes a buckle 140 which is fastened to the ends of the front layer 105 and/or the rear layer 110. According to an embodiment, the buckle 140 includes a standard dress belt tongue-type buckle with a retention bar 145 configured to be inserted into one or more holes 155 in the front 105, rear 110, and/or tourniquet 115 layers, of the type depicted in FIGS. 1-3. In an alternative embodiment, the buckle 140 includes a clamp-type closure mechanism, of the type depicted in FIG. 4. It is noted, however, that any suitable form of belt retention mechanism or buckle fastening mechanism 140 may be used, while maintaining the function and spirit of the present disclosure.

According to an embodiment, the buckle 140 further includes a ratchet mechanism 150. According to an embodiment, the belt retention mechanism 140 is coupled to the ratchet mechanism 150 via a quick release mechanism 160. The quick release mechanism 160 aids in the quick removal of the tourniquet belt system 100 from the wearer, enabling the tourniquet belt system 100 to more readily be applied to a patient as a tourniquet. For example, when the tourniquet component 120 aspect of the tourniquet belt system 100 is needed, the belt retention mechanism 140 can be removed in one motion with the quick release mechanism 160. This in turn leaves the ratchet mechanism 150 still attached to the tourniquet belt system 100. In alternative embodiments, the ratchet mechanism 150 may be integral with the belt retention mechanism 140.

Referring now to FIG. 4, a tourniquet belt system 100 having a front layer 105 and a rear layer 110 separated is illustratively depicted, in accordance with an embodiment of the present disclosure.

According to an embodiment, the tightening rod 135 is concealed between the front layer 105 and the rear layer 110. The front layer 105 and the rear layer 110 may be partially or entirely separable, enabling a user to access the tightening rod 135 to be uses for constricting the tourniquet around the wounded area of the patient. According to various embodiments, the tightening rod 135 may be locked in place using an attached loop. According to various embodiments, the tightening rod 135 may be positioned within a compartment 165 between the front layer 105 and the rear layer 110 which is configured to house the tightening rod 135. According to an embodiment, the portion of the front layer 105 and the rear layer 110 at which the tightening rod 135 is housed may be coupled using a fastening mechanism such as, for example, a snap fastener 130, a hook and loop fastener, a magnet, and/or any other suitable type of fastener. In certain embodiments, all or a portion of front layer 105 may be separable from rear layer 110 and may optionally be formed in multiple segments, with at least the segment housing compartment 165 being separable from rear layer 110.

According to various embodiments, the front layer 105 and the rear layer 110 are configured to be jointly worn as a belt and tucked into the belt loops in a suitable article of clothing. According to other embodiments, the rear layer 110 is configured to be tucked into the belt loops in a suitable article of clothing and the front layer 105 is configured to be coupled to the rear layer 110 over the belt loops via one or more securing mechanisms such as, for example, hook and loop fasteners, snap fasteners, and/or any other suitable form of fastener. According to various embodiments in which the front layer 105 is coupled to the rear layer 110 over the belt loops, the tourniquet layer 115 may be housed entirely within and/or to the front layer 105. For example, in the event that a tourniquet is needed, rather than pulling the entire tourniquet belt system 100 through the belt loops, the front layer 105 is pulled off of the real layer 110, along with the tourniquet layer 115, enabling the tourniquet to readily be applied to a patient's wound.

Once removed from the wearer, the belt component formed by the front 105 and rear 110 layers and the tourniquet layer 115 is looped around a wounded area of a patient on which the tourniquet is to be applied and pulled through the ratchet mechanism 150, and the tightening rod 135 is twisted, constricting the tourniquet layer 115 and reducing bleeding of the patient. In preferred embodiments, the tourniquet belt system 100 includes a rod securement mechanism 170 that holds the tightening rod 135 in position. The rod securement mechanism 170 may be any suitable securement means that functions to secure the tourniquet layer 115 in a tightened position when the tourniquet is in use, while also not interfering with the function and appearance of the system as a traditional belt when the tourniquet is not in use. In a preferred embodiment the rod securement mechanism 170 is a loop of suitable material or fabric. When the system is worn as a traditional belt, the loop may be used to receive and hold against the wearer's body the excess material of the belt, as with a traditional belt. When the tourniquet is in use, the loop may be used to receiving an end of the tightening rod 135 to prevent un-twisting of the tourniquet layer 115.

In certain situations, wearers of the tourniquet belt system 100 may have equipment, tools, or accessories affixed to the belt during ordinary wear. For example, first responders such as police officers, firefighters, and emergency medical personnel commonly have equipment fastened to their belts. Needing to remove such equipment from the tourniquet belt system 100 prior to use would reduce the life-saving quickness that the system is designed to provide. Therefore, alternative embodiments of the tourniquet belt system 100 provide for an outer layer that has suitable attachment mechanisms for an equipment layer, such as hook and loop enclosures or snap fasteners. In a preferred embodiment, the outside of front layer 105 is partially, substantially, or entirely covered by an outer securing mechanism 107, e.g., hook and loop enclosures (e.g. Velcro®), permitting an equipment or accessory belt layer to be affixed over top of the tourniquet belt system 100. For example, the outside of front layer 105 may comprise loop portions of the hook and loop enclosures while the inside of the accessory belt may comprise hook portions of the hook and loop enclosures. In this manner, a wearer may wear the tourniquet belt system 100 through the belt loops on their pants and affix an accessory belt over top of the tourniquet belt system 100. In an emergency situation where the tourniquet is required for use, the wearer can readily remove the accessory belt along with all of the associated accessories and access the tourniquet belt system 100, without the need for individually removing each accessory.

Referring now to FIG. 5, a flowchart of a method 500 for using a tourniquet belt system is illustratively depicted, in accordance with an embodiment of the present disclosure.

At 505, a user unfastens the tourniquet belt system, enabling the tourniquet belt system to be removed from the user. According to various embodiments, the tourniquet belt system includes a belt strap component, which includes a front layer and a rear layer. The front layer and the rear layer are coupled to each other using a belt strap fastening mechanism. The tourniquet belt system further includes a tourniquet component, concealed between the front layer and the rear layer, which includes a tourniquet layer secured to an inner portion of the belt strap component, which runs along a length of the belt strap, and a tightening rod. According to some embodiments, the tourniquet layer is not secured to the inner portion of the belt strap component, enabling the tourniquet layer to be removed from the belt strap component. A portion of the tourniquet layer is coupled to the tightening rod such that twisting the tightening rod decreases a length of the tourniquet layer within the belt strap component. The tourniquet belt system further includes a buckle component which includes a belt fastening mechanism for fastening the belt strap around a user, and a ratchet mechanism configured to secure the belt strap component around a surface.

According to various embodiments, the buckle component further includes a quick release mechanism configured to separate the fastening mechanism from the belt strap component. According to these various embodiments, unfastening the tourniquet belt system from the user includes applying the quick release mechanism in order to separate the fastening mechanism from the belt strap component.

At 510, the belt strap, which has been unfastened and removed from the user, is wrapped around a wounded area of a patient. Once wrapped around the wounded area, a first end of the belt strap component, at 515, is pulled through the ratchet mechanism, forming a tight seal around the wounded area of the patient.

According to various embodiments, the belt strap component further includes a compartment for concealing the tightening rod. The front layer and the rear layer are configured to separate as a location of the compartment, enabling the user to access the tightening rod. The user, at 520, separates the front layer from the rear layer at the location of the compartment, revealing the tightening rod.

Once the user gains access to the tightening rods, the user, at 525, twists the tightening rod, constricting blood flow to the wounded area.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A tourniquet belt system adapted to be worn by a user, comprising:

a belt strap component comprising a front layer and a rear layer, the front layer having a compartment having an elongate opening, the compartment comprising a cavity integrated into the front layer, and wherein the front layer and the rear layer are selectively coupled with a belt strap fastening mechanism, the compartment being concealed when the front layer is in a first position of use with an inner surface thereof abutted against an inner surface of the rear layer;

a tourniquet layer concealed between the front layer and the rear layer when the first layer is in the first position of use, the tourniquet layer being associated with the rear layer and extending substantially along a length of the belt strap component;

a tightening rod coupled to the tourniquet layer such that the tightening rod is only exposed when the front layer is separated from the rear later, and wherein twisting the tightening rod decreases a length of the tourniquet layer within the belt strap component, the tightening rod configured to fit entirely within the compartment when the front layer is in the first position of use;

a buckle component interconnected to a first end of the belt strap component, the buckle component having a buckle fastening mechanism for fastening the belt strap component around the user; and a ratchet mechanism configured to receive a second end of the belt strap component, secure the belt strap component around a surface, and to selectively tighten the belt strap component.

2. The tourniquet belt system as recited in claim 1, wherein the buckle component further includes a quick release mechanism configured to separate the buckle fastening mechanism from the belt strap component.

3. The tourniquet belt system as recited in claim 1, wherein the front layer is at least partially comprised of leather.

4. The tourniquet belt system as recited in claim 1, wherein the front layer and the rear layer are configured to selectively separate at a location adjacent to the compartment, enabling the user to access the tightening rod.

5. The tourniquet belt system as recited in claim 1, wherein the tourniquet layer is at least partially comprised of nylon.

6. The tourniquet belt system as recited in claim 1, wherein the belt strap fastening mechanism is selected from the group consisting of: one or more snap fasteners, one or more hook and loop fasteners, and thread.

7. The tourniquet belt system as recited in claim 1, wherein the belt strap component includes one or more holes configured to receive a portion of the buckle fastening mechanism.

8. The tourniquet belt system as recited in claim 1, wherein the front layer includes an outer securing mechanism configured to enable an equipment layer to be fastened against an outer portion of the front layer.

9. The tourniquet belt system as recited in claim 1, wherein the cavity is in the form of a socket with walls that correspond to an outer perimeter of the tightening rod.

10. A method adapted for applying a tourniquet to a patient, comprising:

providing a tourniquet belt system comprised of:

a belt strap component comprising a front layer and a rear layer, the front layer having a compartment having an elongate opening, the elongate opening comprising a cavity integrated into the front layer, and wherein the front layer and the rear layer are selectively coupled with a belt strap fastening mechanism, the compartment being concealed when the front layer is in a first position of use with an inner surface thereof abutted against an inner surface of the rear layer;

a tourniquet layer that is concealed between the front layer and the rear layer when the first layer is in the first position of use, the tourniquet layer being associated with the rear layer and extending substantially along a length of the belt strap component;

a tightening rod coupled to the tourniquet layer such that the tightening rod is only exposed when the front layer is separated from the rear later, and wherein twisting the tightening rod decreases a length of the tourniquet layer within the belt strap component, the tightening rod configured to fit entirely within the compartment when the front layer is in the first position of use; and a buckle component interconnected to a first end of the belt strap component, the buckle component having a buckle fastening mechanism for fastening the belt strap component around a user; and a ratchet mechanism configured to receive a second end of the belt strap component, secure the belt strap component around a surface, and selectively tighten the belt strap component;

unfastening a tourniquet belt system from the user by removing the belt strap component from the buckle component;

wrapping the belt strap component around a wounded area of the patient;

pulling the first end of the belt strap component through the ratchet mechanism, forming seal around the wounded area;

employing the ratchet mechanism to incrementally tighten the belt strap component;

transitioning the front layer to the second position of use to expose the tightening rod; and twisting the tightening rod to constrict the wounded area.

11. The method as recited in claim 10, wherein the buckle component further includes a quick release mechanism configured to separate the buckle fastening mechanism from the belt strap component, and wherein unfastening the tourniquet belt system from the user includes applying the quick release mechanism to separate the buckle fastening mechanism from the belt strap component.

12. The method as recited in claim 10, wherein the tourniquet layer is at least partially comprised of nylon.

13. The method as recited in claim 10, wherein the belt strap fastening mechanism is selected from the group consisting of: one or more snap fasteners, one or more hook and loop fasteners, and thread.

14. The method as recited in claim 10, wherein the belt strap component includes one or more holes configured to receive a portion of the buckle fastening mechanism.

15. The method as recited in claim 10, wherein the cavity is in the form of a socket with walls that correspond to an outer perimeter of the tightening rod.

16. A tourniquet belt system adapted to be worn by a user, comprising:

a belt strap component comprising a front layer and a rear layer, the front layer having a compartment having an elongate opening, and wherein the front layer and the rear layer are selectively coupled with a belt strap fastening mechanism, the compartment consisting of a cavity integrated into the front layer that is concealed when the front layer is in a first position of use with an inner surface thereof abutted against an inner surface of the rear layer;

a tourniquet layer that is concealed between the front layer and the rear layer when the first layer is in the first position of use, the tourniquet layer being associated with the rear layer and extending substantially along a length of the belt strap component;

a tightening rod coupled to the tourniquet layer such that the tightening rod is exposed only when the front layer is separated from the rear later, and wherein twisting the tightening rod decreases a length of the tourniquet layer within the belt strap component, the tightening rod configured to fit entirely within the compartment when the front layer is in the first position of use; and a ratchet mechanism configured to receive a second end of the belt strap component, secure the belt strap component around a surface, and to selectively tighten the belt strap component.

17. The belt system of claim 16, wherein the cavity is in the form of a socket with walls that correspond to an outer perimeter of the tightening rod.

* * * * *